United States Patent [19]

Chang et al.

[11] 4,282,079

[45] Aug. 4, 1981

[54] PLANAR GLASS ION-SELECTIVE ELECTRODE

[75] Inventors: Jack C. Chang, Webster; James R. Sandifer, Rochester, both of N.Y.

[73] Assignee: Eastman Kodak Company, Rochester, N.Y.

[21] Appl. No.: 121,080

[22] Filed: Feb. 13, 1980

[51] Int. Cl.³ ............................................. G01N 27/36
[52] U.S. Cl. ................................................ 204/195 G
[58] Field of Search ................ 204/1 T, 1 A, 195 G, 204/195 P, 195 M

[56] References Cited

U.S. PATENT DOCUMENTS

| | | | |
|---|---|---|---|
| 3,260,661 | 7/1966 | Kemp et al. | 204/197 |
| 3,649,506 | 3/1972 | Petersen et al. | 204/195 G |
| 3,700,577 | 10/1972 | Grauer | 204/195 G |
| 3,718,569 | 2/1973 | Petersen et al. | 204/195 G |
| 3,856,649 | 12/1974 | Genshaw et al. | 204/195 F |
| 4,053,381 | 10/1977 | Hamblen et al. | 204/195 M |
| 4,073,052 | 2/1978 | Szonntagh | 204/195 F |
| 4,133,735 | 1/1979 | Afromowitz et al. | 204/195 G |

FOREIGN PATENT DOCUMENTS 1596982 7/1971 Fed. Rep. of Germany ...... 204/195 G

OTHER PUBLICATIONS

Jap. 79035-798 (English abstract).

Primary Examiner—G. L. Kaplan
Attorney, Agent, or Firm—J. Jeffrey Hawley

[57] ABSTRACT

A planar glass ion-selective electrode is described comprising an inherently conductive internal reference electrode, a cation-selective glass membrane and means for adhering the reference electrode to the glass membrane. The thickness of the glass membrane is uniform in regions intended for contact with a sample for analysis.

The glass electrode is useful in assaying for the presence of sodium, hydrogen, potassium and other cations present in samples such as blood, urine, plasma, and serum.

10 Claims, 2 Drawing Figures

PLANAR GLASS ION-SELECTIVE ELECTRODE

BACKGROUND OF THE INVENTION

1. Field of the Invention

This invention relates to analytical measurement and in particular to planar, glass electrodes for determining cation concentrations in solution. More specifically, this invention relates to multilayer elements for use in the potentiometric determination of ion activity in aqueous liquids, particularly body fluids such as blood sera.

2. Description of Related Art

The related art is replete with a great variety of electrode types and structures for the measurement of various ions in solution. Typically, devices for obtaining such measurement of various ions in solution include a reference electrode and a separate ion-selective electrode. When simultaneously immersed into the same body of solution to be analyzed, the reference and ion-selective electrodes constitute an electrochemical cell, across which a potential develops. This potential is proportional to the logarithm of the activity of the ion of choice which is related to concentration in the solution of the ion of choice to which the ion-selective electrode is sensitive. The foregoing relationship between the potential and ionic activity in solution is described by the well-known Nernst equation. An electrometric device, usually either a direct reading circuit or a null-balance potentiometric circuit, is employed for measuring the potential between the electrodes.

Historically, the ion-sensitive electrode generally comprised an electrode body (usually some type of glass container) containing a known reference solution in contact with a half-cell of known potential, generally Ag/AgCl/"XMCl" and an ion-selective polymeric or glass membrane. The membrane was mounted in an aperture in the electrode body in such a fashion that, when the electrode was immersed in the unknown solution, the membrane contacted both the reference solution within the electrode body and the unknown solution. An appropriate metal probe coated with a layer of an insoluble salt of the metal immersed in the contained reference solution served as the contact while providing a reference potential for the electrode. The selectivity of the electrode was determined by the composition or components of the membrane. Such electrodes are referred to herein as "barrel" electrodes. U.S. Pat. Nos. 3,598,713; 3,502,560; and 3,562,129 provide detailed descriptions of electrodes of this type.

Major shortcomings of some conventional ion-selective electrodes include:

(1) cost: generally a single electrode can be quite expensive;

(2) reproducibility: even with the most carefully performed conditioning procedures, after the first use of the electrode to determine the ionic activity of fluids such as body fluids, the exact composition of the electrode membrane (glass or polymeric) is unknown due to the potential for contamination by earlier test solutions, and for this reason the results are often suspect.

(3) bulk: the barrel electrodes are quite bulky and require a large surface area for operation.

The foregoing problems have been solved to a significant extent by the recent development of dry-operative multilayer ion selective electrodes (ISEs) as described in U.S. Pat. No. 4,214,968 issued July 29, 1980, in the name of C. J. Battaglia et al. These electrodes comprise a dried internal reference electrode in contact with a non-glass hydrophobic ion-selective membrane. The multilayer ISE electrodes described in Battaglia et al can be planar and of uniform thickness in regions of the membrane intended for contact with a sample for analysis. An advantage of the Battaglia dry-operative ion-selective electrode includes its capability of manufacture in a size such as that of a conventional photographic slide transparency. Thus the electrode—or "slide" as it is often referred to—can be low cost and disposable after single use. A glass-membrane containing electrode with at least those advantages would be desirable. The dried internal reference electrode of Battaglia et al is typically composed of one or more dried layers that generally demonstrate minimal, if any, measurable conductivity. In this regard, it will be appreciated that all components in an electrode must be conductive during measurement to provide measurable potential difference representative of chemical activity of species in a liquid under analysis. In the dry operative electrode of Battaglia et al, although the so-called dried layers prior to sample spotting are non-conductive, the sample liquid permeates the membrane and dried layers. Components in the dried layers, for example elctrolyte salts, combine with permeated liquid to provide the necessary conductivity. The internal reference electrode of the present invention, however, must be inherently conductive prior to sample application.

U.S. Pat. Nos. 3,649,506 and 3,718,569, issued Oct. 14, 1969 and Feb. 27, 1973, respectively, describe "solid-state" glass electrodes in which a conductor having a surface layer of an electrochemically active metal is coated with a first coating of a mixture of a molten glass and a halide of the active metal. A second outer coating of molten ion-selective glass is coated over the first coating. The two coatings are thereby bound cohesively to each other. Unfortunately, the high temperatures required to melt and coat the molten glass renders the technique impractical for the preparation of electrodes having components affected by high temperature. Plastic supporting members and other addendum therefore, may be destroyed during the application of molten glass coatings.

SUMMARY OF THE INVENTION

According to the present invention, there is provided a planar ion-selective glass electrode comprising an inherently conductive reference electrode adhered to a cation-selective glass membrane of predetermined uniform thickness in regions intended for contact with a sample for analysis. The ion-selective glass electrode further comprises means for adhering the inherently conductive internal reference electrode to the glass membrane. An optical support for the electrode can also be provided. Polymeric supports such as poly(ethylene terephthalate) are particularly preferred.

The inherently conductive reference electrode can comprise either a metal/metal-salt/electrolyte reference half-cell or a single or multiple-layer redox couple reference electrode.

The cation-selective glass membrane can comprise a homogeneous glass membrane or heterogeneous glass membrane. In the latter case, a matrix of low electrical conductivity containing particles of finely divided cation selective glass is contemplated.

The cation sensitive glass can be sensitive to hydrogen or other monovalent cations such as potassium or lithium. A preferred embodiment includes a sodium selective homogeneous glass membrane.

The means for adhering the glass membrane to the cation selective glass electrode can comprise a conductive adhesive layer interposed between the glass membrane and the conductive reference electrode. Alternatively, the reference electrode itself can include adhering means, such as pressure-sensitive adhesive admixed with the electrolyte, the admixture serving to adhere the reference electrode to the glass membrane. Various materials can be employed as adhering means and are described below.

A method for determining specific ion activity or an aqueous liquid using the glass ion-selective electrode in accordance with the present invention comprises applying a sample of the aqueous liquid on the glass cation-selective membrane and measuring the potential exhibited by the ion-selective electrode.

It is expected that electrodes described herein generally can produce concentration determinations which demonstrate a coefficient of variation of less than about 10%, preferably less than about 3%.

DESCRIPTION OF THE PREFERRED EMBODIMENTS

Figure 1:
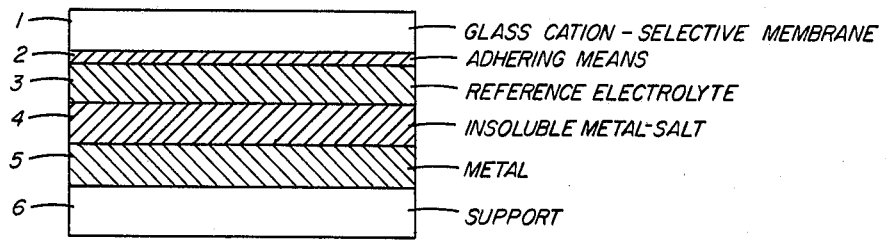
FIGS. 1 and 2 are cross-sectional views of ion-selective electrodes as described herein.

As described hereinabove, previous so-called "solid-state" or glass membrane electrodes include component layers that are applied from a molten state, or include complex arrangements for containing internal reference electrolyte solutions which render the disposability of the latter economically undesirable. The planar glass ion-selective electrodes of the present invention avoid the need for coating of molten glass layers and containment of internal solutions. This is achieved principally with a glass ion-selective electrode comprising a cation-selective glass membrane adhered to an inherently conductive reference electrode by an adhering means. The glass electrode which is in planar format and of uniform glass membrane thickness in regions intended for contact with a sample for analysis is easy to use.

The ion-selective electrodes of the present invention have a solid integral appearance and require only a drop (i.e., below about 50 μl and preferably about 10 μl) of solution to produce a useful measurement. Measurements can generally be made in reasonable time, less than five minutes being desirable. Because of their low cost, the electrodes of this invention can be discarded after a single measurement, thereby avoiding contamination due to prior use. This would insure integrity of the non-selective membrane for each new measurement.

Although the layers described hereinafter are generally referred to as being "coated" one over another, it should be understood that the term "coating" is meant to include laminating or otherwise depositing the various strata one over another, as well as actually coating using conventional coating, dipping, or extrusion techniques to achieve layering of the various strata.

The glass ion-selective electrodes of the present invention comprise:

(a) an inherently conductive internal reference electrode, (b) adhered to the reference electrode, a glass cation-selective membrane of predetermined uniform thickness in areas thereof intended for contact with a test solution, (c) means for adhering the glass membrane to the internal reference electrode, and (d) an optional support.

The term "thin", when used in reference to individual layers of preferred embodiments of the electrodes of the present invention, describes individual electrode layers having a maximum thickness of about 50 mils. Preferably, such "thin" layers are on the order of less than about 10 mils in thickness. Most preferred are layers on the order of less than about 2 mils.

The term "uniform" when used herein in reference to the thickness of the ion-selective glass membrane describes a predetermined thickness tolerance in regions of the layer intended for contact with a sample analysis. This tolerance, if not met can cause non-uniform determinations of potential related to activity from test to test on successive glass ion-selective electrodes. Uniformity of thickness will generally call for a maximum variation in the thickness of the membrane of at most about 20% in regions thereof intended for contact with a sample for analysis.

The term "inherently conductive", when used in connection with the reference electrode and, when necessary or desirable, the adhering means of the present invention describes a sufficiently low (bulk) resistivity to permit measurement of potential difference attributable to the chemical activity of a species in a liquid sample applied to the outer surface of the glass-membrane. Such low resistivity must be inherent, moreover, as liquid from the sample applied to the glass membrane cannot permeate into the internal reference electrode as in the Battaglia et al dry-operative non-glass electrodes. The determination of whether a candidate for the internal reference electrode is inherently conductive, therefore, can entail (a) the tentative assembly of a glass membrane, and internal reference electrode, (b) application on the glass membrane of a liquid sample containing cations in a predetermined dynamic concentration range and to which the glass membrane is selective, and (c) potentiometric measurement of the cell designated reference electrode/membrane/sample/membrane/reference electrode using any conventional potentiometric measuring device.

If a measurable reading is obtained for cations in that dynamic range, the internal reference electrode is inherently conductive.

Alternatively, the internal reference electrode can be evaluated without the glass or sample solution. This will entail potential measurement of the cell designated reference electrode/reference electrode. Again, if a measurable reading is obtained, the internal reference electrode is inherently conductive.

Of course, if no measurable reading is obtained according to either evaluation, the internal reference electrode is not inherently conductive.

Inherently Conductive Reference Electrode

As with any ion-selective electrode useful in the determination of ionic activity and consequently ionic concentration in solution, the electrodes of the present invention have an internal reference electrode which exhibits a reproducible reference potential against which the potential occurring at the interface between the ion-selective electrode and the solution and an external reference electrode under test can be measured. The reference electrode herein is internal and is inherently conductive before contact with a sample for analysis.

Figure 2:
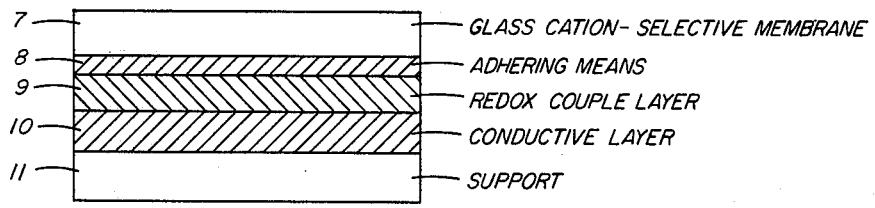

According to the present invention, the reference electrode can be of two distinct types, both of which exhibit the required fixed potential necessary to achieve useful results. The useful reference electrodes are:
(1) metal/metal-salt electrodes (see FIG. 1), and
(2) redox couple electrodes (see FIG. 2).

Metal/Metal-Salt Electrodes

A useful conductive internal reference electrode comprises a metal in contact with an insoluble salt of the metal which can in turn be in contact with an electrolyte, i.e., a conductive matrix containing the anion of the salt. A very commonly used such element is represented as Ag/AgCl/"XMCl$^-$" (XMCl$^-$ indicating Cl$^-$ in a known concentration).

According to the present invention, the metal/metal-salt reference electrode comprises a conductive layer of a metal in conducting contact with a layer of a salt of the metal as used in known electrodes and a conductive electrolyte layer in contact with the metal-salt layer.

The conductive metal layer can comprise any suitable conductive metal of the well-known types which have been used in such electrodes, and which is compatible with the structure, particularly the formats described herein. Particularly useful conductive metal layers include suitably thin layers of silver, nickel, and platinum.

The salt layer in contact with the conductive layer can comprise substantially any insoluble salt of the metal of the conductive layer which establishes a fixed interfacial potential with the metal of the conductive layer. Such layers, which are well known and thoroughly described in the aforementioned patents and publications, generally comprise a salt of the metal which is a product of the oxidation of the metal, as, for example, AgCl, Hg$_2$Cl$_2$, etc. A highly preferred embodiment of the present invention utilizes the aforementioned well-known Ag/Ag$_n$X (wherein X=S$^-$, Cl$^-$, Br$^-$ or I$^-$, and n=1 or 2) interface to establish the potential of the reference electrode. Electrode elements of this type can be prepared using a number of well-known techniques which include, by way of example, dipping a layer of silver as a foil or supported thin layer into a solution of molten silver halide. According to a preferred embodiment of the present invention, the silver-silver halide couple can be produced by vacuum depositing silver onto a suitable support of the type described below, preferably an insulating film, and then chemically converting a surface stratum of the silver layer to silver halide. Generally techniques for chemically converting metal to metal halide involve exposure or contact of the surface of the metal, in this case silver, with a solution of a salt of the halide to be formed in the presence of an oxidant for a period and at a temperature sufficient to cause the desired conversion. Typical conditions for this sort of chemical conversion are well known, and examples of simple and preferred techniques are shown in the examples below. Other useful techniques for preparing such electrodes are described in U.S. Pat. Nos. 3,591,482 to Neff et al issued July 6, 1971, 3,502,560 to Wise issued Mar. 24, 1970, and 3,806,439 to Light et al issued Apr. 23, 1974. Although the teachings of all of these references are directed primarily to the preparation of wire electrodes, the application of ordinary engineering skill will render their application to the manufacture of electrodes constructed on thin films of polymeric support apparatus. Alternatively, a discrete layer of silver halide may be coated over the silver layer so long as appropriate contact between the silver and silver halide is maintained.

Although it is possible to obtain the metal/metal-salt interface with substantially any ratio of metal layer to salt layer thickness, in a preferred embodiment which assures a sufficiently dense layer of metal salt it is preferred that the insoluble metal-salt layer have a thickness equal to at least 10% of the overall thickness of the conductive metal layer. According to a preferred embodiment of the present invention wherein a surface layer of a vacuum-deposited silver layer is converted to a suitable salt, from about 10 to about 20% of the thickness of the silver layer is converted to silver salt using chemical conversion techniques.

The second member of the metal/metal-salt conductive reference electrodes of the present invention comprises the conductive electrolyte layer. According to a preferred embodiment of the present invention, the electrolyte layer can comprise hydrated gel, hydrated polyvinyl alcohol, a hydrophobic ion exchange resin or the like, provided the layer is conductive. See, for example U.S. Pat. No. 3,856,649.

The conductive electrolyte layer of the present invention comprises a binder and a salt. According to a preferred embodiment, the anion of the salt is common to the salt of the metal-salt layer and at least a portion of the cation of said salt comprises the ion which the electrode can detect.

The binders for the conductive reference electrode may comprise polymeric latices, for example those described in U.S. Pat. Nos. 3,411,911 and 3,411,912. Polymers in these patents are water-insoluble, water-permeable interpolymers exhibiting salt tolerance, dimensional stability, and desirable adhesive characteristics. The interpolymers comprise acrylic acid, unsaturated carboxylic acid ester, and sulfobetaine units.

Suitable binders for the conductive reference electrolyte solution may comprise any material suitable for the formation of continuous, coherent, cohesive layers compatible with the salt of the electrolyte layer and, if formed by coating, a solvent system for both the ionic salt and the polymeric binder. Preferred materials of this type are natural and synthetic polymeric film-forming materials such as hydrated forms of polyvinyl alcohol, gelatin, agarose, deionized gelatin, polyacrylamide, polyvinyl pyrrolidone, hydroxyethyl acrylate, hydroxyethyl methacrylate, polyacrylic acid, etc. Specifically preferred from among these materials are the hydrated hydrophilic colloids such as hydrated gelatin (especially deionized gelatin), agarose, polyvinyl alcohol and hydroxyethyl acrylate.

In selecting a binder for the electrolyte layer, a prime consideration is that the binder and included electrolyte be conductive or otherwise pretreated during manufacture such as by hydration to become conductive.

The ionic salt which is included in the polymeric binder will be determined by the composition of the metal/metal-salt portion thereof. For example, in a potassium selective electrode which uses AgCl as the insoluble metal salt, potassium chloride is a logical choice although sodium chloride, etc. may also be used. For sodium ion determinations in a similar configuration, sodium chloride would be useful, etc. Thus, the salt will generally be a water-soluble salt having cation selected from ammonium, alkali metals and alkaline earth metals, mixtures of same or any other suitable cation to which the electrode responds, and as anion a halogen or sulfur depending upon the composition of the metal-salt layer. Conductive metal salts of these anions are commonly insoluble.

Appropriate solvents for the polymeric binder and ionic salt will depend largely on the nature of the polymer and the salt. Generally, polar solvents suitable for dissolving the salt and the polymer are satisfactory. Thus, water is a preferred solvent for layers of hydrophilic materials such as polyvinyl alcohol and gelatin.

Since the thickness of the electrolyte layer will to some extent determine the response characteristics of the electrode, it is generally desirable to maintain the layer rather thin. Layers having dry thicknesses on the order of from about 0.1 to about 0.5 mil are useful. A preferred thickness is about 0.2 mil. Where electrode response characteristics are not critical, the thickness of the layer may vary over a wide range and only the application of sound engineering skills and the use requirements of the finished electrode will determine its limits.

The concentration of ionic salt in the conductive electrolyte layer may also be varied widely, depending upon response time desired, etc. and especially the level or amount of polymer used. In the preferred embodiments described herein wherein the binder level ranges from about 2.4 to about 10 g/m$^2$, the concentration of the salt ranges from about 1.4 to about 2.5 g/m$^2$. Concentrations of salt outside these ranges may be similarly useful. Generally, salt concentrations of from about 20 to about 40 percent by weight total solids in the layer are preferred.

In an alternative embodiment useful metal/metal salt (specifically Ag/AgX) reference electrode elements can be prepared using techniques common to the manufacture of photographic film.

According to such procedures either or both of the metal (i.e., silver) and metal salt (i.e., silver halide) are prepared by coating suitable silver halide photographic emulsions and processing as required. For example, a useful silver halide layer can be prepared applying to a vacuum deposited silver layer by coating a conventional fine grain silver chloride-gelatin emulsion at coverages of from 0.054 to 0.54 g/m$^2$ of gelatin and 1.16 to 1.83 g/m$^2$ of silver as silver chloride.

Useful silver layers which can be overcoated with silver halide layers as just described may be prepared by coating a poly(ethylene terephthalate) support with a layer of fine grain silver chloride, gelatin emulsion at a coverage of 2.02 g/m$^2$ of silver as silver chloride and 95 mg/m$^2$ of gelatin using conventional photographic film manufacturing techniques. The silver chloride layer is then developed for five minutes in a standard black-and-white developer solution known as Kodak Developer D-19 at room temperature and under white light conditions. After thorough washing and drying, this layer is overcoated with a silver chloride emulsion as just described.

Useful electrodes may also be obtained by coating the silver chloride emulsion over evaporated layers of gold, copper and nickel and using fine grain silver bromide emulsions to prepare the metal salt layer.

Oxidation-Reduction Electrodes

The second type of internal reference electrode useful in the successful practice of the present invention is the so-called oxidation-reduction electrode (hereinafter called redox electrode). Redox electrodes have been described and generally include an inert metal wire dipping into a solution containing two different oxidation states of a chemical species. An example of such an electrode comprises a platinum wire dipping into a solution containing ferrous and ferric ions. Such a cell is abbreviated Pt/Fe$^{+2}$, Fe$^{+3}$. The electrode reaction is Fe$^{+3}$+e$^-$⇌Fe$^{+2}$. Redox electrodes can also be made with organic molecules that can exist in two different oxidation states. The most widely used of this type is the so-called quinhydrone electrode in which the redox system is:

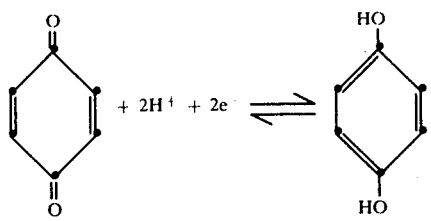

and the cell is represented as:

PT/QH$_2$, Q, H$^+$

Conductive redox electrodes of this type can also be prepared in a "solid-state" format to provide the conductive internal reference element of the composite ion-selective electrodes of the present invention.

The conductive redox electrode of the present invention comprises:
(a) a solid, electrically conductive layer in contact with
(b) a redox couple.

The redox couple may be dissolved or dispersed in the electrically conductive layer or be provided as a discrete conductive solid layer comprising the redox couple dissolved or dispersed in a suitable binder and in conducting contact with the conductive layer.

The Conductive Layer

The conductive layer of the redox reference electrode comprises an electrically conductive material or conductor (as this term is conventionally understood in the art). It will be appreciated that the conductive material should not interact with the redox composition except in the desired and controlled electrochemical fashion required for operation of the electrode, i.e., to establish a reproducible reference potential. Useful results have been obtained with such inert conductors as carbon, platinum, gold and nickel. So long as the conductor is selected so that no unstable electrochemical or other undesired interaction with the redox couple is observed, the choice is not critical. A particularly useful conductor is carbon, for example, particulate carbon.

In certain embodiments, as in the case of carbon where the inert conductor may be in the form of discrete conductive particles, it may be necessary that such particles be maintained in electrically conductive contact in a solid layer by means of some binder or matrix. The binder may comprise any material which permits intimate particle-to-particle contact and conductive contact between the conductor and the redox couple as described hereinafter. Generally, such binders comprise relatively low concentrations of hydrophilic polymers such as gelatin, polyvinyl alcohol, and polyvinyl pyrrolidone. It is, however, possible to use hydrophobic polymers such as silicone rubber for the binder. Whatever the binder used, the ratio of conductor-to-binder must be sufficiently high that the resistance of the layer is low enough to insure adequate electrical conductivity. Such resistances are obtainable with weight ratios of conductor-to-binder of between about 1:1 and 3:2.

The Redox Couple Composition

The redox couple composition comprises the soluble redox couple and whatever other means are required to maintain the composition in a solid form. This other means generally comprises a matrix or binder of one sort or another which contains the redox couple as a solid solution or dispersion.

The redox couples of the present invention, as alluded to above, comprise pairs of the same chemical species (usually ions) in differeing oxidation states.

The formal potential of the reference electrode of the present invention, i.e., the electrical potential of the redox couple at equal concentrations of its reduced and oxidized components at some defined finite value of ionic strength, is determined by:

(1) the redox couple chosen, and
(2) The ratio of activities of oxidized-to-reduced components.

According to a preferred embodiment of the present invention, the ratio of the oxidized to the reduced component (i.e., the molar ratio of material in one oxidation state to material in the other oxidation state) is about unity (1). At this ratio, the redox buffer capacity is largest. Of course, depending upon the type of measurement to be made using the electrodes described herein, this ratio may be varied quite broadly.

In use the redox couple must be capable of establishing a reproducible interface with the conductive layer to establish a reproducible potential; i.e., the redox couple must be capable of exchanging electrons with the conductive layer in a constant fashion when the potentiometric circuit is completed. It is important that the conductive layer and the redox couple together poise the potential of the redox chemistry in a fast electrochemical exchange reaction between the redox couple and the conductor. It is this capability to establish a reproducible potential which is referred to herein as the "compatibility" of the redox couple with the conductive layer. A redox couple which readily establishes such a fixed potential with a given conductor is said to be "compatible" therewith.

According to a preferred embodiment, it is desirable in order for the electrode to possess an extended shelf-life capability, that the oxidized and reduced forms of the couple be stable for the desired shelf-life.

Redox couples which are particularly useful in the successful practice of the present invention include ferric/ferrous ion couples such as $Fe(CN)_6^{-3}/Fe(CN)_6^{-4}$ and cobaltic/cobaltous couples such as $Co(terpyridyl)_2^{+3}/Co(terpyridyl)_2^{+2}$ wherein terpyridyl is 2,6-di-2'-pyridylpyridine.

Any redox couple capable of exchanging electrons with a compatible conductive layer and sufficiently stable against aerial oxidation as to provide a useful shelf-life is useful in the successful practice of the invention.

Although some redox couples may be applied as a solid layer directly to the conductive layer without a matrix or binder, in view of the high solubility of many of the useful redox couples and the difficulty with which materials of this type are applied to the conductive layer in their solid form (i.e., as crystals, etc.), it is generally desirable to apply redox couples as a dispersion or solution in a suitable compatible binder or matrix.

The preferred matrixes for the redox couple comprise a hydrophilic colloid such as gelatin, polyvinyl alcohol, polyacrylamide, polyvinyl pyrrolidone, etc., which colloid is most preferably inherently conductive.

It is also possible to use such hydrophobic materials as cellulose acetate or poly(n-butyl methacrylate-co-2-acrylamido-2-methylpropane sulfonic acid-co-2-acetoacetoxyethyl methacrylate) can be used as the binder or matrix for the redox couple.

Although the redox reference electrodes are generally prepared in a two-layer configuration (i.e., a solid layer of inert conductor in conducting contact with a superimposed solid dried redox couple layer), it has also been found that both the inert conductor and the redox couple may be incorporated into a single layer to provide a useful electrode. In this configuration, it is preferred to use a hydrophilic matrix of the type described above in connection with the redox couple layer for the combined layer; however, hydrophobic binders are also useful. Embodiments of single-layer reference electrodes are described in the Examples below. The techniques for their preparation and use are identical to those of the two-layer or double-layer electrodes described herein.

The choice of application method, and binders employed for the redox electrode is dictated by the requirement that the electrode be inherently conductive as defined. Thus, if necessary, pretreatment such as hydration or otherwise during manufacture is contemplated to confer conductivity upon the layer(s) of the resultant electrode.

Glass Cation-Selective Membrane

The cation-selective glass membrane employed in the practice of this invention can be selected from many well-known materials. The glass membrane, moreover, is planar in configuration; i.e., it is flat and exists without sidewalls such as are present on containers or receptacles composed of glass.

Among the patents and publications which describe such useful glass cation-selective materials, the following are illustrative, the contents of which are incorporated herein by reference to the extent that they are pertinent:

U.S. Pat. No. 4,133,735 to M. A. Afromowitz et al, issued Jan. 9, 1979;

U.S. Pat. No. 3,718,569 to A. J. Peterson et al, issued Feb. 27, 1973;

U.S. Pat. No. 3,649,506 to A. J. Peterson et al, issued Mar. 14, 1972;

U.S. Pat. No. 4,181,579 to C. L. Booth, issued Jan. 1, 1980;

U.S. Pat. No. 4,052,285 to J. V. Dobson, issued Oct. 4, 1977; and

Z. Stefanac and W. Simon, *Anal. Letters,* 1(2), 1–9 (1967).

Ion-selective glass membranes can be selected that exhibit specificity for any one of the monovalent cations $H^+$, $Na^+$, $K^+$, and $Li^+$. Depending on the ion to be detected by the electrode of this invention, the ion-selective glass, for example, may be any one of the following: soda glass, borosilicate glass, a mixed alkali lead glass, a ternary glass, lithia glass, alkali-silicate glass, and an alkali-alkaline earth glass or alumina-silicate glass.

The ion-selective material may be sensitive to the $H^+$ ion, in which case the following glasses may be used: Corning triple purpose glass (27 to 29 mole % $Li_2O$, 2 to 4 mole % $Cs_2O$ and/or $Rb_2O$, 4 to 7 mole % $La_2O_3$, 1 mole % $UO_2$, and balance ($SiO_2$)); Corning 015 glass (22 mole % $Na_2O$, 6 mole % $CaO$ and 72 mole % $SiO_2$); or Perley glass (65% $SiO_2$, 28% $Li_2O$, 4% $La_2O_3$, and 3% $Cs_2O_3$ by weight).

In another form the glass ion-selective membrane may be sensitive to $Na^+$ ions and in this case the ion-selective material may be a finely-divided soda glass, for example a glass which is similar to Corning 015 glass, having the following composition: 21.4% $Na_2O$, 6.4% $CaO$, and 72.2% $SiO_2$ by weight.

Ternary glasses may be used for detecting different ions. Such glasses may contain $SiO_2$ and $Na_2O$ or $Li_2O$ together with one of the following compounds: $K_2O$, $SnO_2$, $B_2O_3$, $ZnO_2$, $Al_2O_3$ and $Ga_2O_3$. Alternatively suitable ternary glasses include three compounds each chosen from a different one of the following four groups (a) to (d):

Group (a) $Sb_2O_3$, $TiO_2$, $ZrO_2$, $GeO_2$, $SnO_2$, and $PtO_3$;
Group (b) $CaO$, $MgO$, and $BeO$; Group (c) $La_2O_3$, $Nb_2O_3$, and $Y_2O_3$; and
Group (d) $Al_2O_3$, $B^2O^3$, $Ga_2O_3$, and $Fe_2O_3$.

Each glass used in the present ion-selective electrode preferably has an electrical specific resistivity of less than $10^{12}$ Ohm centimeters.

Ternary glasses containing oxides of elements of the fourth and fifth groups of the periodic table, such as $SnO_2$, $ZrO_2$, and $TiO_2$ may be used to form electrodes sensitive to the $K^+$ and $Na^+$ ions. Similarly, ternary glasses containing oxides of trivalent elements such as $La_2O_3$ and $Y_2O_3$ may be used in making $Li^+$-sensitive electrodes. Other glasses suitable for use in making such electrodes sensitive to the ions mentioned above and other ions will be found in the book "Glass Electrodes for Hydrogen and other Cations", edited by George Eisenman 1967 published by Edward Arnold.

A preferred ion-selective glass for the membrane of the present invention comprises a sodium-selective multi-component glass composed of $SiO_2$ (69 mole %), $Li_2O$ (11%), $Al_2O_3$ (12), $B_2O_3$ (6%), $Ga_2O_3$ (2%). Other sodium-selective glasses that can be used are referred to in Z. Stefanac and W. Simon, *Anal. Letters*, 1(2), 1–9 (1967), or can be glasses in the $Na_2O$-$Al_2O_3$-$P_2O_5$ system as disclosed in U.S. Pat. No. 4,181,579 to C. L. Booth issued Jan. 1, 1980.

As used herein, the term "glass membrane" when used in connection with the cation-selective glass membrane of the present invention decribes a homogeneous glass layer composed entirely of glass. The membrane can also be a heterogeneous glass layer composed of a matrix of low electrical conductivity material containing particles of a suitable cation-selective glass. Suitable matrices comprising such glass particles are described in U.S. Pat. No. 4,052,285 to J. V. Dobson, issued Oct. 4, 1977. The thickness of the cation-selective glass membrane will affect electrode response and it is preferred to maintain the thickness of this layer below about 5 mils. The uniformity of thickness of the glass cation-selective membrane plays an important role in the optimum utilization of electrodes of the type described herein.

Adhering Means

In accordance with this invention, means for adhering the cation-selective glass membrane to the conductive reference electrode is provided. Such means can be provided, for example, by a discrete layer composed of material having adhesive qualities sufficient to adhere the glass membrane to the conductive reference electrode. A preferred adhesive material is a pressure-sensitive material, particularly one that can tolerate electrolyte salts.

Pressure-sensitive adhesives that may be useful can consist of a tacky resin or polymer, on an intrinsically non-tacky polymer or elastomer can be tackified by the addition of a tacky resin or plasticiser. Suitable tackifiable polymers are, e.g., natural unvulcanized rubber, synthetic rubber such as polyisobutylene; polychloroprene; polybutadiene; polyacrylonitrile; and copolymers of these with styrene and styrene homologues and acrylic monomers; polyvinyl acrylate and its copolymers and polybutyl methacrylate; and vinyl acetate polymers.

Tacky and tackifying resins for use as the adhesives are, e.g., rosin and rosin derivatives such as hydrogenated rosin esters and alcohols, liquid polymer styrene and styrene homologues; polymerised terpenes such as α-pinene; ketone resins; low molecular weight polyisobutylenes and other olefins.

If required, at tack-controlling agent may be added, preferably in the form of a soft or easily deformable material to allow good flow and contact with the receiving surface. Particularly suitable materials are long-chain hydrocarbons containing 12 or more carbon atoms such as paraffin and polyethylene waxes, fatty acids and their derivatives, and polyethylene glycols.

Other pressure-sensitive adhesives which may be employed are described in Bolduc U.S. Pat. No. 3,907,557, issued Sept. 23, 1975; Bergstedt et al U.S. Pat. No. 2,953,475, issued Sept. 20, 1960; and Reed U.S. Pat. No. 3,257,228, issued June 21, 1966.

Alternatively, the adhering means may comprise a layer of a low temperature heat-cured conductive adhesive. The composition may be made of carbon particles dispersed in a thermosetting plastic composition. When heated by induction, heat generated in the composition is confined to localized regions around the carbon particles, thereby curing the plastic and bonding the glass membrane to the conductive reference electrode. Suitable other bonding compositions employed to join materials exhibiting bonding incompatibility are described in U.S. Pat. No. 3,900,360 to A. F. Leatherman, issued Aug. 19, 1975. According to the latter patent, a bonding composition incorporates a susceptor material that responds to indirectly applied energy such as an alternating magnetic or electric field to produce internal heat.

The adhering means may also be incorporated in the electrolyte layer of the conductive reference electrode of the present invention. Thus, as previously indicated, the electrolyte layer may comprise an adhesive binder such as a three-part interpolymer of acrylic acid, unsaturated carboxylic acid ester and a sulfobetaine as described in U.S. Pat. Nos. 3,411,911 and 3,411,912.

It is also contemplated that adhesives can be employed in the glass membrane layer, particularly glass membranes composed of finely-divided glass in a low-conductivity binder as described elsewhere herein.

The adhering means may also appear simultaneously in more than one location of the present glass ion-selective electrode. Thus, two or more of an adhesive layer, the electrolyte layer containing an adhesive, and the glass membrane layer containing an adhesive can be employed, so long as inherent conductivity is retained between the glass membrane and the reference electrode in the region of the ion-selective electrode intended for sample analysis.

Alternatively, mechanical adhering means can be employed that serve to clamp the glass membrane to the reference electrode. Such clamping may be provided in regions not intended for contact by a sample for analysis.

Support

According to preferred embodiments, the glass ion-selective electrodes of the present invention include a support which may be comprised of any material capable of bearing, either directly or by virtue of some intervening adhesion-improving layer, the other necessary portions of the electrode. Thus, the support may comprise ceramic, wood, glass, metal, paper, or cast, extruded, or molded plastic or polymeric materials, etc. The composition of the support is relatively unimportant, so long as it is capable of carrying the overlying electrode components and it is inert; i.e., it does not interfere with the indicating potentials observed as, for example, by reacting with one of the overlying materials in an uncontrolled fashion. In the case of porous materials such as wood, paper, or ceramics, it may be desirable to seal the pores before applying the overlying electrode components. The means of providing such a sealing are well known and no further discussion of the same is necessary here. Electrically insulating supports are preferred although, as described hereinafter, metallic conductive supports which serve multiple purposes are equally useful and may in fact simplify the structure of the electrode.

According to a highly preferred embodiment of the present invention, the support comprises a sheet or film of an insulating polymeric material. A variety of film-forming polymeric materials are well suited for this purpose, such as, for example, cellulose acetate, poly(ethylene terephthalate), polycarbonates, polystyrene, etc. The polymeric support may be of any suitable thickness, typically from about 2 to about 20 mils. Similarly thin layers or surfaces of other materials mentioned above could be used. Methods for the formation of such layers are well known in the art.

In certain cases, a separate and distinct support need not be provided. Such a case occurs when one or more layers of the electrode demonstrate sufficient mechanical strength to support the remaining portions of the electrode. For example, when a metal-insoluble metal-salt electrode is used as the internal reference electrode, as described below, the metal layer may be in the form of a self-supporting foil. The metal foil serves as the support, an integral portion of the internal reference electrode, as well as a contact for the electrode.

Preparation of the Electrode

The solid-state electrodes of the prior art are commonly manufactured using a conductive wire as the starting material and dipping the wire sequentially into generally highly viscous solutions of the components of the individual finished electrode layers to construct a bulbous multilayer "solid-state" electrode. See, for example, U.S. Pat. No. 3,856,649. Alternatively, as shown in U.S. Pat. No. 3,649,506, individual layers of ion-selective glass are applied over the tip of a conductive wire. In either of these situations, the resulting ion-selective membrane is of relatively non-uniform thickness in those areas intended for contact with an aqueous solution whose ionic activity is to be determined.

Electrodes of the present invention are prepared by coating, laminating or otherwise applying the various individual layers one over another in any conventional fashion.

Thus, (FIG. 1) a typical manufacturing procedure for a metal-insoluble metal-salt reference element electrode would involve chemically converting or otherwise applying a layer of an insoluble metal salt (4) to a layer of a compatible conductive metal (5) in the form of a coating on a nonconductive substrate or a metallic foil on a support (6), overcoating the metal-salt layer with a reference electrolyte solution layer (3), overcoating the electrolyte layer with an adhering means layer (2) and overcoating or laminating over with a glass cation-selective membrane (1) to provide a complete electrode. Alternatively, the layers can be laminated so long as intimate contact between layers is achieved and maintained, and uniformity of thickness of the glass cation-selective membrane is attained.

Coating of the various electrode layers provides a simple yet efficient method for preparing electrodes as described herein. Using well-known techniques, the various layers can be deposited under very carefully controlled conditions which provide highly accurate layer composition and layer thickness, which are extremely important to the successful preparation of electrodes as described herein. Once prepared by coating, which will take place in a planar or substantially planar configuration, if the electrode has been prepared on pliant support, it may be configured into almost any useful geometry by cutting, bending, etc. which will permit contact of the ion-selective membrane with a test solution. As described below, use of the electrode is in a substantially planar configuration by the application of a drop (less than about 50 $\mu$l) of test solution to the glass ion-selective membrane. A particularly useful mount for making measurements in this configuration is described in U.S. Pat. No. 4,053,381 entitled "Device for Determining Ionic Activity of Components of Liquid Drops".

Electrodes using redox reference elements are prepared using techniques similar to those described above for the metal-insoluble metal-salt reference electrodes. Thus, (FIG. 2) the inert conductive layer (10), which may be a metal foil or, alternatively, a dispersion of a particulate conductor such as carbon on a support (11), is coated with a solution or dispersion of the redox couple layer (9), an adhering means (8) applied over the redox species layer, and a glass cation-selective membrane (7) applied thereto as described above. Alternatively, the inert conductor and the redox species may both be incorporated into a matrix or binder composition and a single layer coated to provide the desired reference element. Of course, individual layers may be laminated in conducting contact to provide a similarly useful structure.

Use

The ion selectivity of a glass membrane electrode (ISE) can be observed by measuring the difference in electrical potential between a solution 1 and a solution 2 (both usually aqueous) in the cell arrangement schematically represented by the following:

ISE 1/Solution 1//Solution 2/ISE 2

The calculations required to determine the ionic activity of solution 2 (generally the solution of unknown concentration) are derived from the well-known Nernst equation and are discussed in detail in a paper entitled "Cation Selectivity of Liquid Membrane, Electrodes Based upon New Organic Ligands" of Simon and Morf reported in *Ion-Selective Electrodes*, edited by Pungor, E. Budapest, 1973.

The electrode described herein incorporates within its structure substantially all of the components needed for making a potentiometric determination with the exception of a second reference electrode, the potential-indicating device and associated wiring so that in use the user merely needs to provide for contacting the sample with the glass cation-selective membrane, preferably by application of a small quantity of the sample to be analyzed (on the order of ~50 µl) thereto and connection of appropriate lead wires.

Second reference electrodes such as saturated calomel electrodes for use in combination with the integral electrodes of the present invention are also well known. In addition to such electrodes, reference elements of the type described herein as the internal references may also be used as the second or external reference electrode.

Similarly, potentiometers capable of reading the potentials generated in the ion-selective electrodes of the present invention are well known and, when properly connected as described hereinafter, can be used to give a sensory indication of the potential from which the ionic activity in the unknown solution may be calculated.

The configuration (e.g., physical dimensions such as thickness of the electrode) plays a very significant role in the performance of any specific electrode or set of electrodes. If precise measurements are to be achieved using a series of disposable, single-use planar electrodes, it is important that the thickness of the glass cation-selective membrane be carefully controlled and maintained at some predetermined uniform thickness from electrode to electrode and within regions of a single electrode intended for contact with the test sample.

Minor variations in performance of the present glass ion-selective electrode can be expected. These variations can be compensated for by using either a differential measurement which compares the ion concentration of the unknown sample with that of a similar sample of known ion concentration (i.e., a calibrator or standard) simultaneously applied to an identical electrode, or by initially deriving calibration curves for the electrode for given sets of ambient conditions and subsequently relating the conditions of individual measurements to such calibration curves.

The following examples will serve to better demonstrate the successful practice of the present invention.

Preparation of Ag/AgBr Electrode

Vacuum-deposited metallic silver on polyethylene terephthalate support (~10 mg Ag/dm$^2$) can be prepared. This material is treated for 5 minutes in the following solution:
glacial acetic acid: 0.45 ml
sodium hydroxide: 0.20 g
potassium ferricyanide: 0.80 g
potassium bromide: 2.50 g
distilled water to 1 liter:

The treated material is then washed for 5 minutes in running distilled water.

Visual inspection will reveal the occurrence of partial conversion to silver bromide, leaving a contiguous layer of metallic silver adjacent the support. A narrow strip along one edge is dipped briefly in a thiosulfate bath to uncover the silver layer for purposes of making electrical contact.

Measurements of the electrochemical response are performed by applying small samples of aqueous solutions varying in Br$^-$ activity to the silver bromide layer. A linear response, with approximately theoretical slope (Nernst equation), can be expected.

Preparation of Ag/AgCl Electrode

An Ag/AgCl half-cell is prepared as described in Example 1 except that the conversion conditions are 30 seconds in a solution containing 8.45 g/l of potassium chlorochromate.

Measurements of electrochemical response are performed to confirm linear potential response with varying Cl$^-$ and Ag$^+$ activity.

EXAMPLE 1

Sodium-Selective Electrode

A silver-silver chloride film on poly(ethylene terephthalate) is prepared as described in preparation of the Ag/AgCl reference electrode [7.6 g/m$^2$ total silver with 15% conversion to AgCl (1.16 g/m$^2$)]. A latex of a sulfobetaine interpolymer as described in any one of examples 1–5 of U.S. Pat. No. 3,411,912 is prepared. A composition of the interpolymer including NaCl is coated over the AgCl layer at a coverage of 1.5 g NaCl and 5 g interpolymer. A uniformly thin homogeneous sodium selective glass membrane is laminated directly to the electrolyte latex layer. The sodium-selective glass contemplated comprises SiO$_2$ (69 mole %), Li$_2$O (11%), Al$_2$O$_3$ (12%), B$_2$O$_3$ (6%), Ga$_2$O$_3$ (2%).

The resulting ion-sensitive electrode, represented as Ag/AgCl/latex-NaCl/ion-selective glass membrane can be tested by:

(1) connecting the silver-silver chloride film to the high-impedance input of a potentiometer; and
(2) suspending a drop (25–50 µl) of an NaCl solution to be measured from the tip of a saturated NaNO$_3$ salt bridge connected to an external reference electrode (Hg/Hg$_2$Cl$_2$) which is in turn connected to the reference input of the potentiometer, and contacting the drop to the surface of the electrode. The complete potentiometric cell is represented by:
Hg/HgCl$_2$/NaCl/XM test/ion-selective glass membrane/latex-NaCl/AgCl/Ag.

EXAMPLE 2

Ion-selective Electrode With Pressure-Sensitive Adhesive

The glass ion-selective electrode is prepared as in Example 1 except an inherently conductive pressure-sensitive adhesive layer is interposed between the conductive latex-NaCl layer and the glass membrane.

EXAMPLE 3

A potassium selective glass membrane can be substituted for the sodium-selective glass membrane in Example 2. KCl is substituted for the NaCl mole-for-mole in the electrolyte layer. Useful potentiometric measurements can be expected upon application of a liquid sample containing potassium ions.

EXAMPLE 4

A dry-operative ion-selective electrode can be prepared to demonstrate the effect of a non-conductive internal reference electrode with either a suitable hydrophobic non-glass membrane or a cation-selective glass membrane.

An electrode is prepared as in example 3 of U.S. patent application Ser. No. 893,656 now U.S. Pat. No. 4,214,968 issued July 29, 1980. At the same time an otherwise identical electrode is prepared substituting a potassium-selective glass membrane for the precast membrane described in Ser. No. 893,656. Both electrodes are tested as in example 3 of Ser. No. 893,656. No measurable potentiometric reading is expected for the glass-membrane electrode, whereas measurable readings are obtained in the dry-operative electrode.

Although the multilayer glass electrode elements of the present invention have been described primarily in connection with the potentiometric quantitation of sodium ions, the structures, compositions and techniques described herein are equally applicable to the assembly of electrodes for the analysis of other cations such as $K^+$ $H^+$, and $Li^+$ principally by the selection of appropriate ion-specific glasses for the glass ion-selective membrane, and such electrodes are clearly within the contemplated scope of the instant invention.

Furthermore, it is within the scope of the instant invention to incorporate protective overlayers for the electrode which may serve merely to protect the surface thereof, increase mechanical strength, or serve multiple additional purposes such as permitting selective permeability to a specific ion.

Although the conductive internal reference electrodes of this invention have been described as an exemplified by metal/metal-salt and redox couple electrodes, it will be apparent to the skilled artisan that metal/metal-ion conductive reference electrodes will be similarly useful and ion-selective electrodes incorporating such reference electrode are clearly within the contemplated scope of the appended claims.

While the invention has been described in detail with particular reference to preferred embodiments thereof, it will be understood that variations and modifications can be effected within the spirit and scope of the invention.

What is claimed is:

1. A planar ion-selective glass electrode comprising:
   (a) an inherently conductive internal reference electrode comprising a metal/metal salt reference material, said reference electrode comprising a conducting layer of a metal in contact with a layer of an insoluble salt of said metal, and an inherently conductive adhesive electrolyte layer comprising a water-soluble salt having as an anion the anion of said metal salt layer and a polymeric binder;
   (b) a cation-selective glass membrane of predetermined uniform thickness in regions intended for contact with a sample for analysis; and
   (c) means for adhering said reference electrode to said glass membrane comprising said inherently conductive adhesive electrolyte layer.

2. The electrode of claim 1 wherein said binder comprises an interpolymer comprising acrylic acid, unsaturated carboxylic acid ester, and sulfobetaine units.

3. The electrode of claim 2 further including a support which comprises an electrically insulating polymeric film, said conducting metal layer comprises silver, said layer of insoluble salt comprises a halide salt of silver, and said glass membrane comprises a sodium-selective homogeneous glass membrane.

4. The electrode of claim 1 wherein said binder comprises a member selected from the group consisting of hydrated or otherwise inherently conductive forms of polyvinyl alcohol, gelatin, agarose, polyacrylamide, polyvinyl pyrrolidone, polyhydroxyethyl methacrylate, poly(hydroxyethyl acrylate) and polyacrylic acid.

5. The electrode of claim 1 wherein said layer of insoluble salt comprises a halide salt of said metal.

6. A planar ion-selective glass electrode comprising:
   (a) an inherently conductive redox internal reference electrode comprising an inherently conductive, adhesive redox couple layer comprising a redox couple and a binder over an electrically conducting layer;
   (b) a cation-selective glass membrane of predetermined uniform thickness in a region thereof intended for contact with a sample for analysis; and
   (c) means for adhering said reference electrode to said glass electrode comprising said inherently conductive, adhesive redox couple layer.

7. The electrode of claim 6 wherein said conducting layer comprises a conductor selected from the group consisting of carbon, platinum, and nickel.

8. The electrode of claim 6 wherein said conductor is carbon.

9. The electrode of claim 6 wherein said conducting layer comprises a particulate conductor and a binder.

10. The electrode of claim 9 wherein said particulate conductor is particulate carbon.

* * * * *